US 6,680,166 B1

(12) United States Patent
Mullon et al.

(10) Patent No.: US 6,680,166 B1
(45) Date of Patent: Jan. 20, 2004

(54) DUAL FIBER BIOREACTOR

(76) Inventors: Claudy Jean Paul Mullon, 163 Prospect St., Framingham, MA (US) 01701; Kerry Ann Gagnon, 33 Glendale Dr., Danvers, MA (US) 01923; Christine Marie Tosone, 7 Jersey Way, Walpole, MA (US) 02081; Hugo Osvaldo Jauregui, 25 Bevelin Rd., Providence, RI (US) 02906

(*) Notice: Subject to any disclaimer, the term of this patent is extended or adjusted under 35 U.S.C. 154(b) by 0 days.

(21) Appl. No.: 09/228,382

(22) Filed: Mar. 29, 1999

Related U.S. Application Data

(63) Continuation of application No. 08/837,708, filed on Apr. 22, 1997, now abandoned, which is a continuation of application No. 08/488,185, filed on Jun. 7, 1995, now Pat. No. 5,712,154.

(51) Int. Cl.[7] .................................................. A01N 1/02
(52) U.S. Cl. ......................... 435/2; 435/325; 435/326; 435/378; 435/400
(58) Field of Search .......................... 435/2, 325, 326, 435/343, 378, 400, 297.4, 299.1

(56) References Cited

U.S. PATENT DOCUMENTS 5,622,857 A * 4/1997 Goffe

FOREIGN PATENT DOCUMENTS

GB 2 211 857 A * 7/1989
WO PCT/US94/02140 * 8/1995

* cited by examiner

*Primary Examiner*—David A. Redding
(74) *Attorney, Agent, or Firm*—M. Maus & Associates

(57) ABSTRACT

A cell culture unit is disclosed herewith comprising a shell having two ends with an elongated chamber there between. A liquid and a gas perfusion port are located on each end. Liquid perfusion fibers are connected to the liquid perfusion ports and gas perfusion fibers are connected to the gas perfusion ports. These fibers thereby define an extracapillary and intracapillary space. The cell culture unit further comprises means for communicating with the intracapillary space of the gas perfusion fibers means for communicating with the intracapillary space of the liquid perfusion fibers, and means for communicating with the extracapillary space.

5 Claims, 8 Drawing Sheets

LIVER ASSIST DEVICE PROGRAM
EXTRACORPOREAL CIRCUIT

DUAL FIBER BIOREACTOR

This application is a continuation of application Ser. No. 08/488,185 filed Jun. 7, 1995 now U.S. Pat. No. 5,712,154, and a continuation of application Ser. No. 08/837,708 filed Apr. 22, 1997 now abandoned.

The present invention relates in general to cell culturing systems and specifically to a hollow fiber culturing system and/or ex vivo extracorporeal treatment means which circulates two different types of media, a gas and a liquid.

The most widely used cell culturing systems comprise batch culturing and hollow fiber culturing. Batch culturing comprises growing cells on the interior surface of plastic or glass rollers, or attaching the cells to a flat surface on stationary containers such as petri dishes.

In contrast, hollow fiber culturing systems allow for the in vitro growth of cells on semi-permeable tubular membranes or capillaries. The cells attach to the outer surface of the capillary walls. A nutrient media is circulated through the capillaries to diffuse from the perfusing medium though the capillary walls to the cells. In return, cell products diffuse from the cells through the capillary walls and into the perfusate from which they can be harvested if one so desires. While the prior art is replete with hollow fiber cell culturing systems an in vitro culturing system which is identical to an in vivo system is still illusive Generally speaking, hollow fiber culturing systems encounter three major categories of problems. First, the cells must be supplied with a nutrient media. Second, an optimal and constant environment must be maintained while the cells are metabolizing. Third, a suitable substrate must be available for cell attachment.

One, of the most significant problems within the nutrient category to be overcome in the production of tissue-like derivatives for creating artificial organs via hollow fibers, is oxygenation. Without an adequate oxygen supply, cells cannot metabolize i.e. regulate themselves and grow. The prior art culture systems have supplied oxygen with preliminary perfusion. This oxygenating of the fluid, from outside the fibers is inadequate in that cells prefer a continuous and steady rate of oxygen. Moreover, it is best to supply it directly to the cells and not a distance away. This again is only a mimicking of in vivo conditions where the blood with its hemoglobin carrying molecules bathes cells. In sum, the prior art hollow fiber systems fall short of "bathing" the cells by either supplying an initial non-continuous oxygen perfusion or by doing so at a distance away from the cells.

The prior art has also tried perfusing the media directly with oxygen. However, aqueous nutrient media equilibrated with air is only able to carry 4.5 ml. of oxygen per liter (37° C. 760 mm of Hg). The inability of aqueous solutions to carry oxygen results in oxygen perfusion being the rate limiting step in the culturing process. In order to overcome oxygen shortages the rate must be increased. High circulation rates result in high internal pressures and turbulence. Since cells are quite fragile, vigorous aeration prevents cell propagation and may lead to the denaturation of proteins.

In conclusion, neither pre-oxygenation and/or oxygenating the exterior of the capillaries and/equilibrating the media with air is not optimal. The problem is further compounded when artificial organs are the goal, since all the cells are in a catabolic state and require an even greater amount of oxygen. A discontinuous and/or inadequate and/or turbulent oxygen supply results in a range of cellular problems ranging from irregular cell metabolism and growth to premature death. Thus it is a primary objective of this invention to provide for optimal oxygenation.

Given the aforementioned, it is best to separate the oxygen supply from the medium support. The prior art devices which have done so, employ both a hollow fiber diffusion mechanism and a bath. Either oxygen is diffused through the hollow fiber and the cells are bathed in the medium or the cells are perfused with oxygen and the medium is diffused through the hollow fiber. While this system is quite advantageous, it is difficult to remove products when the hollow fiber is only used for oxygen supply. Conversely, it is problematic for supplying a continuous and steady supply of oxygen, when the hollow fiber only perfuses media and not oxygen. Thus it is a further objective of the present invention to provide for a device which perfuses both a gas and a liquid.

U.S. Pat. No. 4,184,922 employs two perfusion circuits. However, both circuits are perfused with liquid media. It does not perfuse a gas. The patent therefore does not address oxygenation nor improve oxygenation beyond that of the prior art. Moreover, given the dual liquid perfusion, the patent only employs ultrafiltration fibers. The present invention may still be further differentiated in that the dimensions of the present invention's unit range from 7 to 40 cm in length and 1.4 to 5.0 cm in diameter versus the 5 cm long and 0.26 cm diameter unit described in U.S. Pat. No. 4,184,922. Lastly the system described in the aforementioned patent is limited to 50 fibers whereas the present invention may employ up to 7500 fibers thereby increasing the desired product by an extremely advantageous margin. Further advantages of the present invention will become apparent in the remaining specification.

In sum, it is highly desirable to produce a hollow fiber cell culturing system and/or ex vivo extracorporeal blood, plasma and/or serum, treatment unit which overcomes the aforementioned prior art disadvantages.

SUMMARY OF THE INVENTION

The task of the present invention can be solved in an elegant and novel manner by providing for a hollow fiber system wherein some fibers carry a gas and other fibers carry a liquid. More specifically, by providing for a cell culture unit comprising a shell having two ends with a liquid and a gas perfusion port located on each of said end, said ends defining an elongated chamber therebetween. Said cell culture unit further comprising liquid perfusion fibers connected to said liquid perfusion ports and gas perfusion fibers connected to said gas perfusion ports; said fibers defining extracapillary and intracapillary space. Still further said unit comprising means communicating with the intracapillary space of said gas perfusion fibers, means communicating with the intracapillary space of said liquid perfusion fibers and means communicating with said extracapillary space.

BRIEF DESCRIPTION OF THE DRAWINGS

The advantages and features of the present invention will be more fully understood from the following description of the preferred embodiments taken in conjunction with the accompanying drawings wherein.

DESCRIPTION OF THE PREFERRED EMBODIMENT

Figure 1:
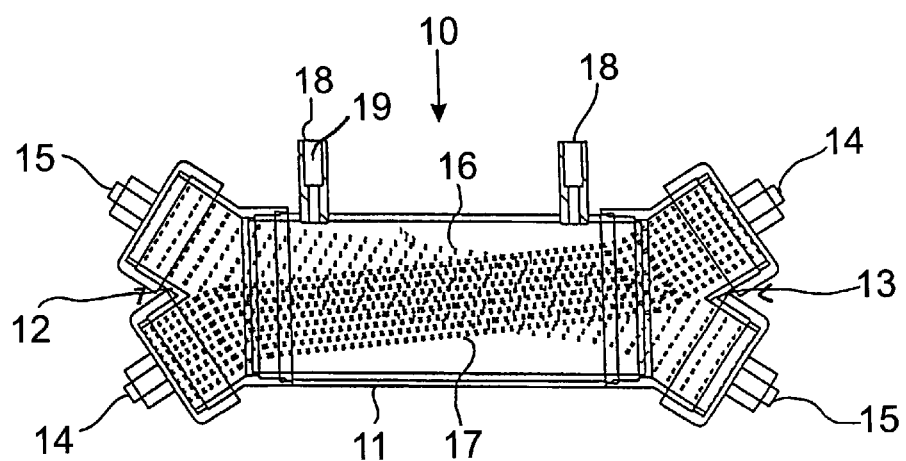
FIG. 1 is a perspective view of a first embodiment of a cell culture unit of the present invention.
Figure 2:
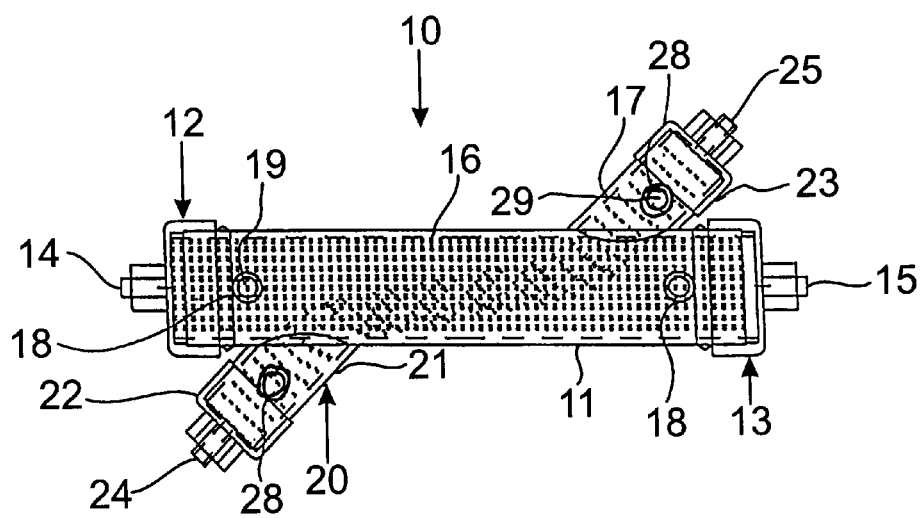
FIG. 2 is a perspective view of a second embodiment of a cell culture unit of the present invention.

In the first embodiment of the present invention as shown in FIG. 1 and FIG. 2, a cell culture unit 10 is provided, having a shell member 11 comprising a first, 12, and second end, 13. Each end bifurcates into two ports, one for liquid perfusion 14, and one for gas perfusion, 15. FIG. 1 specifically illustrates ends 12 and 13 in a Y configuration.

Capillary gas fibers, 16 and liquid perfusion fibers, 17 extend the length of shell, 11. A pair of inoculation ports, 18 of conventional construction are provided to allow access to extracapillary space through holes, 19.

The second embodiment of the present invention shown in FIG. 2 comprises a first cell culture unit 10, having a shell member 11 having a first and second end, 12 and 13 respectively. Said ends comprising an input port, 14, and in exit port 15. Further said shell member 11 is bifurcated by a second cell culture unit, 20, comprising a shell member 21, having first and second ends, 22 and 23 respectively. Said ends comprising input and exit ports 24 and 25 respectively. Notably liquid or gas may be perfused through unit 10 or 20, as long as both are perfused. Similarly, the direction of perfusion is irrelevant. Thus exit and input ports may be serendipitously selected. Accordingly, capillary gas fibers 16 may extend the length of shell 11 and liquid perfusion fibers 17 may extend the length of shell 21, or visa versa. A pair of inoculation ports 18 & 28 are present on each of shells 11 & 21 to allow access to the extracapillary space through holes 19 and 29, respectively.

The shell member 11 and 21 can be made of any of the conventionally available materials, such as glass, polymeric materials, e.g. polyethylene, polysulfone, polystyrene, styrene acrylonitrile, plexiglass, polycarbonate etc. Preferred, however, are clear and durable materials to provide visibility such as polycarbonate, polystyrene, styrene acrylonitrile, plexiglass etc.; and most preferred is polycarbonate.

The dimensions of the shell 11 and 21 may range in length from about 7 cm to about 40 cm, preferably from about 20 cm to about 30 cm and most preferably 25 cm; and in diameter from about 1.4 cm to about 5 cm, preferably from about 2 cm to about 4.5 cm, and most preferably 4 cm.

Ends 12 and 13 may be part of the integral cell unit 10 and 20, (FIGS. 1 and 2) and as such made of the same material. Alternatively they may be separate Y connector end pieces. Said Y end pieces 12 and 13 may be directly attached or connected by means of a connecting sleeve 24 (not shown). If separate, they may be of a material such as standard Pyrex glass Y connectors having dimensions ranging from about 4 cm to about 12 cm, preferably from about 5 cm to about 8 cm and most preferably 6 cm in length; and from about 1.5 cm to about 6 cm preferably from about 2 cm to about 5 cm and most preferably 3 cm in diameter.

Figure 3:
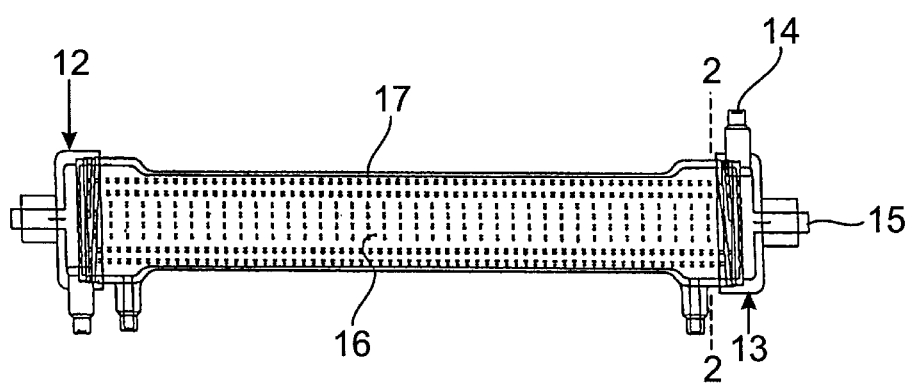
FIG. 3 is a perspective view of a third embodiment.

FIG. 3 depicts a third embodiment of the invention wherein liquid fibers 17 completely surround gas fibers 16. Liquid perfusion port 14 is located perpendicular to gas port 15. Gas is fed through port 15 leading to gas fibers, 16. Liquid is fed through port 14 extending laterally from end 12 and 13, to liquid fibers 17.

Figure 4:
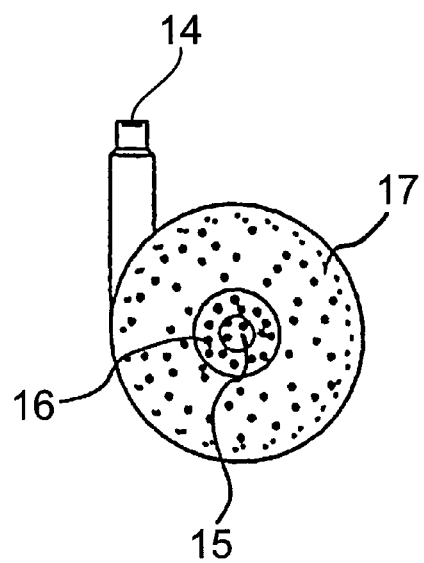
FIG. 4 is a crossectional view alone lines 2—2 of FIG. 3.

FIG. 4 is a crossectional view take n along lines 2—2 of FIG. 3 further illustrating ports 14 and 15 and the internal fiber arrangement.

Figure 5:
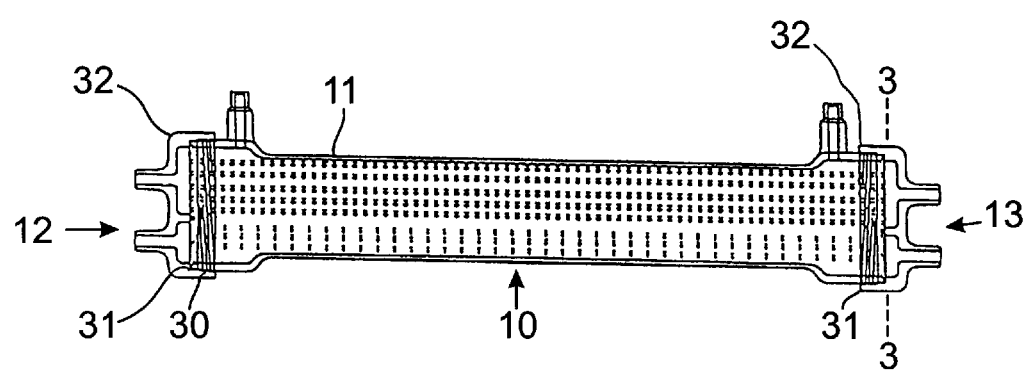
FIG. 5 is a perspective view of a fourth embodiment.

FIG. 5 depicts culture unit 10 having 2 ports at each end in a parallel configuration to each other. Each port in turn defines a separate chamber, 31 and 32 respectively. Ends 12 and 13 may fit into a ring 30, within shell 11, which divides ends 12 and 13 into the two separate chambers, 31 and 32. Notably, while the ports are separated, the gas and liquid perfusion fibers are not separated within unit 10.

Figure 6:
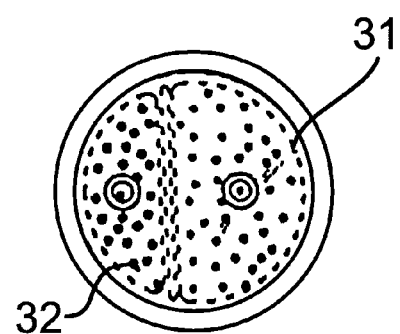
FIG. 6 is a crossectional view along lines 3—3 of FIG. 5.

FIG. 6 is a crossectional view taken along lines 3—3 further depicting the separate oxygen and perfusion ports.

Figure 7:
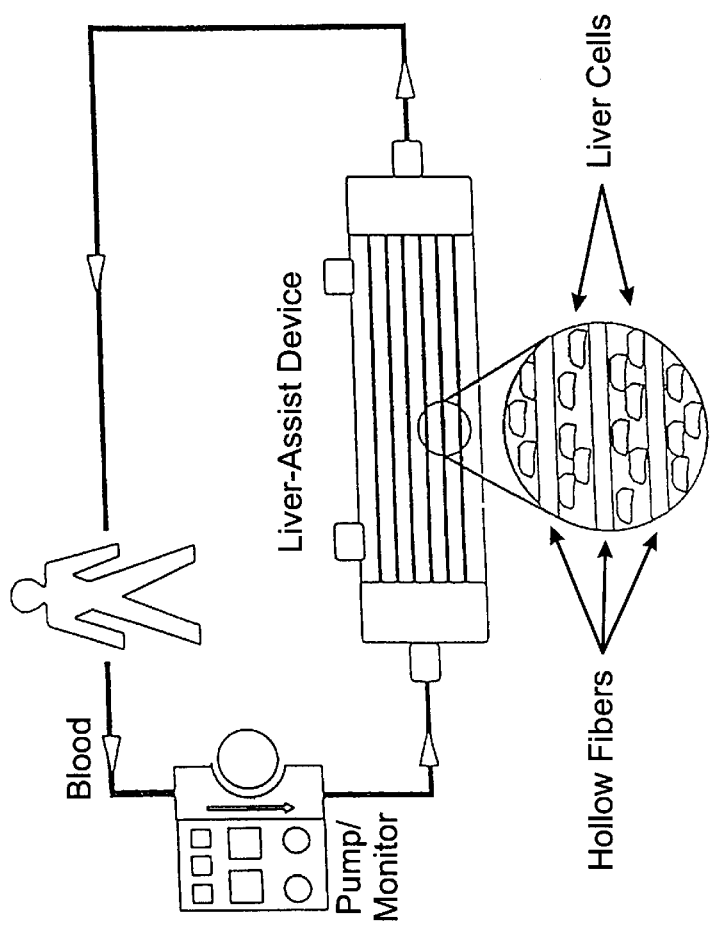
FIG. 7 is a schematic view of an ex vivo extracorporeal blood circuit.

FIG. 7 is a schematic of an extracorporeal circuit incorporating novel culture unit 10. As illustrated blood is circulated from the patient via a pump to unit 10 and back to the patient.

Hollow gas fibers 16 may be manufactured of any conventionally used materials. By way of illustration and not limitation, they may be made of the following materials: polyethylene, polypropylene, etc. Fiber 16 may range in length from about 7 cm to about 40 cm, preferably from about 20 cm to about 30 cm, and most preferably 25 cm. Fiber 16's diameter may range from about 150 um to about 1.5 mm preferably from about 200 um to about 650 um and most preferably 250 um.

Similarly hollow liquid fiber 17 may be manufactured of any conventionally used material. By way of illustration and not limitation, mention may be made of the following materials: polypropylene, polysulfone, cellulose, etc. Fiber 17 may range in length from about 7 cm to about 40 cm preferably from about 20 cm to about 30 cm, and most preferably 25 cm. Fiber 17's diameter may range from about 150 um to about 1.5 mm preferably from about 200 um to about 650 um, and most preferably 250 um.

The culture cell system is assembled in the following manner. Liquid and gas fibers are placed in the shell and attached to their respective input and output ports. If separation of fibers is desired, one may employ a ring as shown in FIG. 4 or employ the Y configuration as shown in FIG. 2. Once secured, the fibers are potted. Any one potting method may be employed. By way of illustration and not limitation mention may be made of the centrifugal potting technique, static potting, etc. Likewise, any number of materials may be used to pot the fibers. By way of illustration and not limitation, mention may be made of polyurethane, epoxy, silicone, etc. Any excess potting material is removed and the end caps are secured. Securing of the end caps may be accomplished via any adhesive or by welding.

The novel culture unit may be employed in a conventional manner with cell suspension media and cells to be cultured being seeded in shell 11 via inoculation parts 28, 18. While all oxygen requiring cell types are contemplated by way of illustration and not limitation mention may be made of various organ cells, including but not limited to hepatocyles and pancreatic cells, as well as all line and stem cells. The novel feature, however, being that gas is supplied to end pieces connected to fibers 16 while liquid is perfused through the end pieces connected to fibers 17. Liquid perfusion may comprise any biological fluid comprising but not limited to culture media, blood (either plasma or serum) urine, sputum, etc. The specific type of liquid and gas perfusion circuits will depend on the particular use of the device, any of which are readily known in the art. One circuit contemplated by the present invention would comprise oxygenation means and medium perfusion means. While the present invention is not limited to any culture medium, mention may be made of Chee's Media, a trademark of the GIBCO Co. and known by the number 93-0165, Dulbecco's Modified Eagle Media, described in GIBCO BRL Life Technologies (1993–1994) Product Catalogue, Minimum Essential Media, described in described in GIBCO BRL Life Technologies (1993–1994) Product Catalogue, etc. The media may be supplemented with any of the known additives including but not limited to insulin, dexamethasone, gentamycin, selinium, transferrin, etc.

Figure 8:
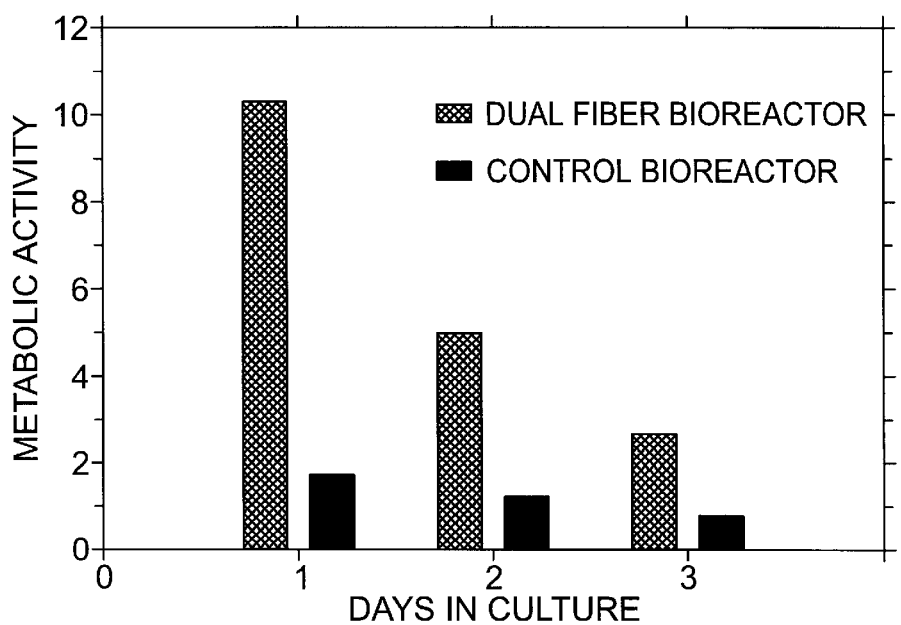
FIG. 8 is a graphical illustration of diazepam metabolic activity of rabbit hepatocytes in bioreactors with different oxygen supplies.

The many advantages of dual hollow fiber perfusion are apparent from FIG. 8. A prior art unit and the present invention culture unit were seeded with 280×10⁶ rabbit hepatocytes and monitored for metabolic activity using diazepam. Both culture units were kept in culture for 3 days with a daily culture media change. The concentration of diazepam metabolites was measured each day. FIG. 8 shows the results.

The dual perfusion unit, i.e. dual bioreactor, of the present invention outperformed the prior art culture unit five times on day 1 and 4 times on days 2 and 3.

Use of the present invention in ex vivo extracorporeal plasma or serum or whole blood treatment may comprise any of the well-known dialyzing techniques. FIG. 7 depicts a typical extracorporeal treatment set up employing the novel unit of the present invention. The unit is advantageously used as follows. Arterial or venous blood or plasma alone, is pumped from the patient through the device at a predetermined rate ranging from about 50 mL to about 1000 mL. The fluid perfuses the bioreactor and returns to the patient thereby advantageously supplying oxygen to the cells within the device.

By way of recapitulation, the present invention comprises a novel dual perfusion culture unit wherein the cells are simultaneously perfused with a gas and a liquid. More specifically, the present invention comprises a cell culture unit comprising a shell having two ends with a liquid and a gas perfusion port located on each of said end, said ends defining an elongated chamber therebetween. Said cell culture unit further comprising liquid perfusion fibers connected to said liquid perfusion ports and gas perfusion fibers connected to said gas perfusion ports; said fibers defining extracapillary and intracapillary space. Still further said unit comprising means communicating with the intracapillary space of said gas perfusion fibers, means communicating with the intracapillary space of said liquid perfusion fibers and means communicating with said extracapillary space. The advantages of this novel unit are readily apparent from the increased metabolic activity of the cells.

Since certain changes may be made without departing from the scope of the invention as described herein it is intended that all matter described in the foregoing specification, including the drawings, shall be interpreted as illustrative and not in a limiting sense.

We claim:

1. A method for culturing cells comprising an extracorporeal circuit comprising the steps of:
   a. seeding a cell culture unit comprising:
      i. a shell having two ends and defining an elongated chamber there between;
      ii. a liquid and a gas perfusion port located on each of said end;
      iii. liquid perfusion fibers connected to said liquid perfusion ports and gas perfusion fibers connected to said gas perfusion ports; said fibers defining extracapillary and intracapillary space;
      iv. communicating with the intracapillary space of said gas perfusion fibers;
      v. means communicating wit the intracapillary space of said liquid perfusion fibers; and
      vi. means communicating with said extracapillary space;
      with cells;
   b. withdrawing blood from a patient;
   c. pumping said withdrawn blood through the liquid perfusion ports of said culture unit while supplying oxygen through said gas perfusion ports;
   d. returning said filtered blood to the patient; and
   e. extracting cells or cellular components.

2. A method for culturing cells comprising an extracorporeal circuit comprising the steps of:
   a. seeding a cell culture unit comprising:
      i. a shell having two ends and defining an elongated chamber there between;
      ii. a liquid and a gas perfusion port located on each of said end;
      iii. liquid perfusion fibers connected to said liquid perfusion ports and gas perfusion fibers connected to said gas perfusion ports: said fibers defining extracapillary and intracapillary space;
      iv. means communicating with the intracapillary space of said gas perfusion fibers;
      v. means communicating with the intracapillary space of said liquid perfusion fibers; and
      vi. means communicating with said extracapillary space;
      with cells;
   b. withdrawing blood from a patient;
   c. separating plasma from blood and its cellular components;
   d. pumping said separated plasma through the liquid perfusion ports of said culture unit white supplying oxygen through said gas perfusion ports;
   e. recombining of plasma with cellular components of blood;
   f. returning said filtered blood to the patient; and
   g. extracting cells or cellular components.

3. The method described in claim 1, wherein the cells to be seeded are hepatocytes.

4. A method for culturing cells or cellular components, comprising:
   a. placing a single bundle fiber of liquid and gas perfusion fibers into a shell consisting of:
      i. two ends and defining and elongated chamber there between;
      ii. a liquid and a gas perfusion port located on each of said end;
      iii. liquid perfusion fibers connected to said liquid perfusion ports and gas perfusion fibers connected to said gas perfusion ports; said fibers defining extracapillary and intracapillary space;
      iv. means communicating with the intracapillary space of said gas perfusion fibers;
      v. means communicating with the intracapillary space of said liquid perfusion fibers; and
      iv. means communicating with said extracapillary space; with cells;
   b. connecting one end of said fibers to input ports and the other end to exit ports located in the shell ends;
   c. potting said fibers;
   d. seeding said chambers with hepatocytes;
   e. perfusing liquid through said liquid perfusion fibers and gas through said gas perfusion fibers;
   f. extracting cells or cellular components.

5. The method of claim 4, wherein the fibers are potted by a centrifugal potting technique.

* * * * *